US009910022B2

(12) United States Patent
Kim

(10) Patent No.: US 9,910,022 B2
(45) Date of Patent: Mar. 6, 2018

(54) REAL TIME OZONE LAYER MONITORING USING ION MOBILITY SPECTROMETRY

(71) Applicant: S. Howard Kim, Charles Town, WV (US)

(72) Inventor: S. Howard Kim, Charles Town, WV (US)

(73) Assignee: Sanghwan Howard Kim, Charles Town, WV (US)

( * ) Notice: Subject to any disclaimer, the term of this patent is extended or adjusted under 35 U.S.C. 154(b) by 259 days.

(21) Appl. No.: 14/802,390

(22) Filed: Jul. 17, 2015

(65) Prior Publication Data

US 2017/0016868 A1    Jan. 19, 2017

(51) Int. Cl.
   *G01N 24/00*    (2006.01)
   *G01N 33/00*    (2006.01)
(52) U.S. Cl.
   CPC ..... *G01N 33/0039* (2013.01); *G01N 33/0052* (2013.01); *G01N 33/0059* (2013.01)
(58) Field of Classification Search
   CPC .......................... G01N 21/03; G01N 33/0039
   USPC ...................... 250/371, 372; 356/319, 437
   See application file for complete search history.

(56) References Cited

U.S. PATENT DOCUMENTS

| | | | | |
|---|---|---|---|---|
| 4,652,761 A * | 3/1987 | Kerr | ........................ | G01J 3/32 250/372 |
| 5,218,416 A * | 6/1993 | Haring | ................. | G01N 21/274 250/252.1 |
| 5,767,519 A * | 6/1998 | Gelbwachs | ........ | G01N 21/3504 250/338.5 |
| 7,489,397 B2 * | 2/2009 | Acevedo | ................ | G01N 21/33 250/339.05 |
| 8,823,938 B2 * | 9/2014 | Beck | .................... | G01N 21/314 356/432 |

* cited by examiner

*Primary Examiner* — Nina Bhat

(57) ABSTRACT

The present invention provides a capability of Ion Mobility Spectrometry/Atmospheric Pressure Ionization Mass Spectrometry (IMS/MS) in the negative ion mode for Ozone detection and methods for ozone layer depletion monitoring in laboratory environment. Ammonium hydroxide vapors, as a dopant chemical, introduced to the inlet system of the IMS/MS interfaced with the reaction sphere enables ozone ionized to be $O_3^-$. The data obtainable from proposed methods show how ozone is depleted and which compound affect the most for $O_3$ destruction among the $O_3$ depletion substances of Chloro Fluoro Carbons (CFCs), Hydro Fluoro Carbons (HFCs), Hydro Chloro Fluoro Carbons (HCFCs), Hydro Chloro Bromo Carbons (HCBCs), and Hydro Chloro Iodo Carbons (HCICs). Based on the results obtainable, more likely the IMS alone system without coupling with the mass spectrometer (IMS/MS) will rather be selected to develop as a spatial real time ozone layer depletion monitor. Real time monitoring device of ozone concentration in ambient atmospheric conditions can also be developed with this technique.

1 Claim, 4 Drawing Sheets

REAL TIME OZONE LAYER MONITORING USING ION MOBILITY SPECTROMETRY

BACKGROUND OF INVENTION

The ozone layer depletion (OLD) in the stratosphere is a rather old theme which was found early 1970s. A large loss of total ozone as ozone hole in *Antarctica* pole was found by Farman et al. in 1985 [1]. This observation triggered international effort to prevent the ozone layer from further depletion. Scientists starting from F. Sherwood Roland and Mario Molina (Novel prized later 1996) successfully established a mechanism of ozone layer depletion chemistry [2]. This situation led the Montreal Protocol in 1987 and its revisions in 1990 (London), 1991 (Nairobi), 1992 (Copenhagen), 1993 (Bangkok), 1995 (Vienna), 1997 (Montreal), 1997 (Kyoto), and 1999 (Beijing). Twenty four nations including the U.S. signed an agreement to freeze the production five different CFCs 1986 levels and to cut the production in half of 1986 level by 1999. A list of ozone depleting substances (ODS) is available, along with their ozone depletion potential (ODP), global warming potentials (GWP) and CAS numbers. (www.epa.gov/science/ozone/ods.html).

Ozone depletion trend amazingly was reported to have got flat since 1995 [3] while National Oceanic and Atmospheric Administration (NOAA) report of Oct. 21, 2011 said ozone hole level in the atmosphere above the South Pole dropped to seasonal low of 102 Dobson Unit October 9 to be the $10^{th}$ lowest point in the 26 years record. Sep. 29, 2013 season high 116 Dobson unit was observed showing improvement but still long way to recover to the level of normal Dobson unit 350 and above. Updated The Antartic ozone hole and where we are now with stratospheric ozone depletion syndrome was reported by Douglass et al. [4]. Laube et al [5] analyzed the firn snow in Greenland and found that $CF_3CCl_3$ and $CF_3CH_2Cl$ continued to increase instead of decrease in the period of 1990s-2012 while $CFCl_2CFCl_2$ and $CF_2ClCCl_3$ decreased slowly. The source of $CF_3CCl_3$ and $CF_3CH_2Cl$ needs to be investigated.

Based on observed variation of chloride decline rate of year to year fluctuation, Strahan et al. [6] predicted the ozone hall shrink will be achieved by 2040. Ozone Depletion free Freon gases such as HCFCs or HFCs were reported to have Ozone Depletion Potential index (ODPI)≤0.002 compared to 1.00 of related ODPI of CFC-11 ($CCl_3F$) [7].

The ionization conditions of IMS and APIMS reaction region and the environment of stratosphere appear to be similar. As a result, studies of electron—molecule reactions that occur in the stratosphere can be simulated with the IMS or APIMS in the laboratory conditions. Simulation test results for the ozone layer depletion occurring in the stratosphere may bring a clearer picture of ozone depletion chemistry in the stratosphere.

Halide Compounds are easily Detected by Electron Capture Detector (ECD). In 1972, J. E. Loblock, who invented ECD for Gas Chromatography (GC), detected CFC-11 ($CCl_3F$) with collaborators in the atmosphere using his ECD-GC [8]. A series of Freon gases including CFC-113 ($C_2F_3Cl_3$) eluted by FID-GC and were identified by both positive and negative product ions by Plasma chromatograph (PC) (early name of IMS) [9]. The reduced ion mobility, $K_0$, of $Cl^-$, $Br^-$, and $I^-$ reported appear to be 2.97±0.02, 2.63±0.02, and 2.53±0.02 $cm^2 \cdot v^{-1} \cdot s^{-1}$ respectively [10,11]. Halide ions were reported with even higher sensitivity were detected with slight amount oxygen doping [12,13] by Atmospheric Pressure Ionization Mass Spectrometry (APIMS).

Although a breakthrough technique of field asymmetry ion mobility (FAIMS) or diffusion mobility spectrometry (DMS) [14-16], which is featured in identification of isomers, isobars, and conformers for the compounds of biologically active molecules, pharmaceuticals, and biomedical compounds, is available and making remarkable progress. Our work however will be done with well established hardware of classic standard IMS-Ni-63. Based on the data from the physical parameter studies [17, 18] to improve the peak to peak resolution and total ion current, the hard ware size evolution was significantly improved and reduced to have total tube Length×Width×Height=13 cm×4 cm×4 cm from a large laboratory scale of original research type instrument of PCP Corporation [19] and believed to be one of the optimal configurations widely used in the IMS/MS system now.

Updated Chemistry of Ozone Depletion. Ozone Layer or Ozonosphere is a layer in the atmosphere which stretches from roughly 10-50 km (or 7-30 miles) above the Earth's surface. It is in between troposphere and stratosphere. Ozone Layer is believed to be formed primarily from interaction between oxygen in its three different forms of $O_2$, O, and $O_3$. i.e. $O_2$ uvc--->2O; $O+M+O_2$--->$O_3+M$ as an exothermic reaction −105 kJ/mol or −25.12 kcal/mol. The updated OLD chemistry was well established [2,20]. That is the CFCs such as $CF_2CL_2$ (Freon 12) and $CFCL_3$ (Freon 11) dissociate to release one odd electron Cl. atom as a free radical by the UV radiation from the Sun. i.e.

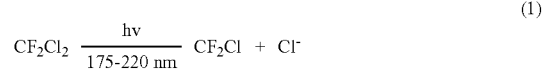

(1)

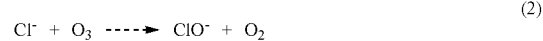

(2)

(3)

Reactions 1,2, and 3 representing how ozone is destroyed producing two odd electron species that is one Cl. atom and one free radical ClO. Reaction 3 may be slower than reaction (2) because it will be dependent upon the concentration of oxygen atom which is less than $O_3$. However ClO. formed thus reacts with atomic state of Oxygen to reproduce Cl. in Reaction 3. This Cl. atom like a catalyst repeatedly is believed to be involved in $O_3$ depletion. Likewise Br, I, NO, OH, undergo $O_3$ depletion reaction by BrO, IO, $NO_2$, and $HO_2$ respectively. Using Eddy diffusion coefficients modeled vertical turbulent motion, calculated life time of CFCs is reported to fall 40-75-140 years [2]. At stratospheric temperature, ClO. reaction with O is reported to be six times faster than the reaction of NO and $NO_2$ with O. As a result, Cl—ClO chain is known to be more effective than the NO—$NO_2$ chain in the catalytic conversion in the Reaction 2 and 3 [2,20].

The estimated photo dissociation rates of $CFCl_3$ and $CF_2Cl_2$ at the altitude of 30 km are reported to be $3\times10^{-7}$ $cm^3$ molecle$^{-1}$s$^{-1}$ and $3\times10^{-8}$ $cm^{-3}$ molecule$^{-1}$ s$^{-1}$ respectively. The peak rate destruction and formation of Cl. occurs at 25-35 km altitudes where the concentration of $O_3$ is high. The troublesome odd electron chain such as OH, $HO_2$; NO, $NO_2$; Cl, ClO can only be terminated by interaction with one another or others to convert to even electron species. Possible termination involving the Cl series with itself Cl.+ClO.--->Cl$_2$O or with one of others i.e. Cl+NO--->NOCl temporarily terminated. However if photolysis takes place, both chains involves in ClO+NO--->Cl+NO$_2$ rather in slow rate. The ClO reaction with NO$_2$ will be rapid:

ClO.+NO$_2$---->ClONO$_2$ (4)

Cl.+CH$_4$---->HCl+CCH$_3$ (5)

Reaction 4 is rapid and 5 is slow but significant reaction to terminate the catalytic chain cycle for Cl. atom. HCl can be formed by reaction 5 in the temporary termination of Cl. atom chain. Whether or not the restarting reaction of OH+HCl--->H$_2$O+Cl. depends primarily on concentration of OH. Photolysis of CFCs including CFCl$_3$ and CF$_2$Cl$_2$ does not occur in troposphere because these molecules are transparent to UV wave length higher range than 290 nm [2]. These mechanisms however were established under the assumption of no free electrons exist in stratosphere.

Electrons in stratosphere. However among solar energetic particles electrons out of Belt radiation so called Relativistic Electrons Precipitation (REP) penetrate deep down to stratosphere [21-22]. The REP can provide a local source of upper stratospheric nitric oxide (NO) which can be formed through between electrons and neutral air at the stratosphere. This nitric oxide plays a major role in the removal of stratosphere ozone as discussed above [23].

Using stratospheric balloon soundings, production of electrons with high energy were observed in stratosphere at latitude 23° South, Longitude 47° West by Van et al [24]. Using a Proton/Electron Telescope (PET), SAMPEX, a comprehensive measurement of energetic electrons was made in 1993 by Cook et al [25]. Multi level, 1-15 Mev, electrons deeply penetrate into atmosphere to be source of ionization in the middle altitude regions.

Since the role of halide compounds in destruction of the stratospheric ozone was discovered, HCFCs (hydrochlorofluorocarbones) have been in use in many applications in place of CFCs. Even though the short life time to reach stratosphere and calculated very low level of ODPI values of HCFCs were reported to be very low [7], sooner or later though HCFCs might be a dominant source of Cl. in stratosphere. As reported by Hossaini [26], the short lived (six months) halogens that is originated from primarily anthrophgenic appear to deplete ozone in the rate half of the CFCs. This HCFCs are not controlled by the Montral Protocol. Short lived HBrFCs was reported to have 3.6 times higher than that of HCFCs. This issue was reported to be discussed at the Montreal Protocol meeting, April 2015, in Bankock on the substances that deplete the ozone layer [27]. Cicman et al [28] in their electron/molecule beam study, found the energy (0-8.6 eV range) needed for associative or dissociative electron attachment at gas temperature 300° K. Four fragment negative ions of Cl$^-$, F$^-$, CClF$^-$, and CF$_2^-$ were observed. This is similar energy range to the electron energy level emanating from the Ni-63 isotope of IMS and APIMS ionization source at ambient temperature. Thus depending on the electron density flux, electrons are involved in e-ion-molecule reactions with halides in the stratosphere.

If electrons are available in stratosphere, one expects the interaction between electrons and chemicals such as CFCs, HCFCs, NO$_x$, CO$_x$, H$_2$O, and other air constituents in that environment. In an effort to see interaction between electrons and Cl., electrons were intentionally shot up to stratosphere 40 km high altitude and treated data by computer simulation. The electron capture by Cl. to react with O$_3$ i.e. Cl$^-$+O3--->ClO$^-$+O$_2$. This reaction is believed not to be as favorable as the reaction (2) due to the EA of Cl>EA of ClO. Boosting electron affinity (EA) by hydrated Cl$^-$, (H$_2$O)Cl$^-$, to 4.6 eV level from 3.6 eV the reaction type of (2) is even harder [29]. (See Table 1). As a result, we prevent the Cl. from being a catalyst in the reaction (2). Relativistic electron flux at 50 km high altitude was reported to be 800/cm$^3$ [30].

TABLE 1

Electron Affinities of Related Molecules [31]

| Molecules | Electron Affinity (EA eV) |
|---|---|
| NO$_3$ | 3.073 |
| Cl | 3.611 |
| F | 3.399 |
| Br | 3.364 |
| CO$_3$ | 3.260 |
| I | 3.059 |
| I$_2$ | 2.520 |
| Br$_2$ | 2.420 |
| Cl$_2$ | 2.400 |
| IO | 2.378 |
| BrO | 2.353 |
| ClO | 2.278 |
| NO$_2$ | 2.270 |
| O$_3$ | 2.103 |
| OH | 1.829 |
| O | 1.462 |
| O$_2$ | 0.452 |

Lu et al [32] reported that the absolute cross sections for dissociative capture of 0 eV electrons to CFCs and HCFCs are strongly enhanced by presence of H$_2$O ice polar stratospheric cloud. The absolute cross sections for CFCl$_3$, CHF$_2$Cl, and CH$_3$CF$_2$Cl were reported to be 8.9×10$^{-14}$, 5.1×10$^{-15}$ and 4.9×10$^{-15}$ cm$^2$ at 0 eV respectively. The value for CFCl$_3$ and CHF$_2$Cl are 1 order of magnitude higher than that in gas phase, while the CH$_3$CF$_2$Cl is 3-4 magnitude higher. The cross section enhancement is interpreted to be due to electron transfer from precursor states of solvated electron in ice to an unfilled molecular orbital of CFCs or HCFCs followed by dissociation. This study indicates that electron induced dissociation on ice is a significant process that lead Cl$^-$ formation after breakup. As a finishing result, this means that the activity is expected to occur slowly than predicted in the O$_3$ destruction process.

In FIG. 1, the ion chemistry of the low atmosphere from the mesosphere to the stratosphere, and the troposphere were summarized [Ref. 33]. In the stratosphere, O$_3$+e-->O$_3^-$ is formed first. By the third body M (O$_2$) subsequently releases O$^-$ e.g. O$_3^-$+O$_2$+M--->O$^-$+2O$_2$, the dissociated oxygen ion, O$^-$, is formed. This atomic state oxygen combine with other oxygen molecule to form O$_3^-$: that is O$^-$+O$_2$--->O$_3^-$. In the upper part of stratosphere as the concentration of CO$_2$, NO$_x$, and SO$_x$ gas increase, O$^-$ ion reacts with these molecules to form CO$_3^-$. NO$_3^-$, and SO$_3^-$ respectively. While the ion chemistries of the lower part of stratosphere and the troposphere progress further into complex terminal particles.

Prior to the time of the ozone destruction reaction mechanism [2] with the above reactions (1-3) were proposed, mass spectrometers were launched into stratosphere using a balloon or rocket platform [34-37]. When negative ions were drawn into a quadrupole mass spectrometer through sampling orifice, O$^-$, NO$_2^-$, and Cl$^-$ (contaminant ? or from CFCs?) were observed at the altitude above 78 km (mesosphere), and CO$_3^-$, HCO$_3^-$, NO$_3^-$, and Cl$^-$ were observed below 78 km. In the mesosphere. When negative ions were again drawn into a quadrupole MS through sampling orifice, OH$^-$, (H$_2$O)CN$^-$, (H$_2$O)NO$_2^-$, (HOCl)NO$_2^-$, (HCN)NO$_3^-$, $(HCl)NO_3^-$, $(HOCl)NO_2^-$, $(H_2O)(HNO_3)NO_3^-$, $(HOCl)NO_2^-$, $(H_2O)(HNO_3)NO_3^-$, $(HOCl)HSO_4^-$, $(HNO_3)(HNO_2)NO_3^-(H_2O)(HNO_3)HSO_4^-$, $(H_2O)(HNO_3)_2NO_3^-$, and $(H_2O)(HNO_3)(H_2SO_4)HSO_4^-$ were observed at 32 to 35 km, and core ions of $NO_3^-$ were observed at 20 to 28 km in the stratosphere. These results coincides with the conclusion of ion chemistry upper atmosphere reported by Smith et al. [33] (see FIG. 1). These results clearly describe that the reaction $O_3^-$ with $CO_2$ to produce $CO_3^-$ with $NO_2$ subsequent reactions producing $NO_3^-$. The significance of increasing greenhouse gas $CO_2$ and $NO_3^-$ effect to ozone depletion cannot be ignored in this regard.

Ozone Measurement Instruments

Since early 1920s the study of ozone concentration in atmosphere instruments have been evolved from ground based spectrometers to balloons, aircraft, rockets, and satellites. These developments have enabled measurements to expand from the atmosphere of isolated ground station to daily global coverage and profiles of ozone in the atmosphere.

Groudbased Measurement. Since 1924, Dobson Spectrometer (Dobsonmeter) by Gordon Dobson [38] and Brewer Spectrophotometer, known as Mark III [39] have been in use as ground based measurement instruments. It measures the total ozone by measuring the relative intensity of the dangerous UVB (305 nm) radiation to the UVA (325 nm) radiation absorbed by the ozone layer using Umkehr method to deduce vertical distribution. However drawbacks are that it is strongly affected by aerosols and pollutants in the atmosphere because they absorb the UV light at the same wave length region. Measurement is usually localized small area. LIDAR [40]. A telescope is used to collect UV light that is scattered by two laser beams one of which is absorbed by ozone (308 nm) and the other is not (351 nm). By comparing the intensity light scattered from each laser, a profile of ozone concentration vs. altitude is measured from 10 to 50 km.

Airborne Measurement. Airborne measurements of ozone provide a direct in situ method of determining ozone concentrations in the atmosphere. Balloons, Rockets, and Aircraft carry instruments into the atmosphere to measure accurate ozone concentration. However, the measurements are made only localized regions and can't provide a global picture of ozone distribution. Balloons [26, 41]. Balloons have been used almost as long as ground devices to measure ozone. They can measure the change in ozone concentration with altitude as high as 25 miles (40 km) and provide several days of continuous coverage and many devises used to measure ozone from balloons so called Ozonesondes. Several instruments can be carried at once and simultaneous measurements of many parameters can be conducted. However since balloons are unpowered flight path cannot be controlled.

Rockets. Rockets measure profiles of ozone levels from the ground to an altitude of 75 km by using photo spectroscopy. Rockets provide all weather capability but are limited by their short life and narrow coverage in geographic range [41].

Aircrafts. Airplanes are used to make detailed measurements of ozone levels and related chemicals in the troposphere and lower atmosphere. Typical missions include 10 or more instruments capable of measuring ozone, chemicals related to the production and destruction of ozone, and atmospheric conditions that affect ozone. In 1987, the Airborne Antarctic Experiment determined that the ozone hole over Antarctica was caused by anthropogenic chlorine. However measurements from aircraft are restricted by concerns for pilot safety, range, and flight duration, and are not continuous [41].

Satellites. Satellites measure over the entire globe every day providing comprehensive data. In orbit, satellites are capable of observing the atmosphere in all types of weather, and over the most remote region on Earth. They are capable of measuring total $O_3$ levels for mapping, profiles, and elements of atmospheric chemistry. Various spectrometers of TOMS (Total Ozone Measurement Spectrometers) were used during 1994-1997 and OMI (Ozone Measurement Instrument) took over the TOMS's roll [39]. Summary of ground level based TOMS and trend of ozone profile measurement was reported [4,42].

Aurora Program. www.esa.int/SPEClALS/Aurora/MZOS39ZAD_0.html, [41]. In 2001, Eropean Space Agency (ESA) was established as a space flight program with first objective of Solar system exploration using robotic spacecraft and human spaceflight. Secondary objective is to search for the life beyond the Earth. This program is a system equipped with four different spectroscopic instruments which are a Infra Red High Resolution Dynamics Limb Sounder (HIRDLS), a microwave emission spectroscopy named Microwave Limb Sounder (MLS), Ozone Monitoring Instrument (OMI) as mentioned above, and a Fourier Transfer Infra Red Spectrometer, named Tropospheric Emission Spectrometer (TES). The technique involved by far is based on the UV-IR absorption or emission spectroscopy [43].

Ion Mobility Spectrometry (IMS)

IMS appears to be another available technique capable to detect $O_3$ and other related gases such as NO, $NO_2$, $NO_3$, $H_2O$, $NH_3$, and $SO_2$, including CFCs, BrFCs, IFCs, HFCs, and HCFCs in the atmosphere with very high sensitivity. The IMS is a technique closely aligned to mass spectrometry which operates at atmospheric pressure conditions [44-49]. It chemically ionizes sample drawn into the reactor with sets of reactant ions (established for by selecting dopant gas or gas phase chemicals), and separates the un-reacted reactant and reacted product ions through a drift tube for detection under atmospheric conditions. The process whereby ions are separated in the drift region is known as mobility. Since mobility depends on collisions of ions with drift gas, it depends also on density as well. Thus the correction of the mobility to standard conditions ($K_0$) will be:

$$\text{Reduced Mobility } (K_0) = K \times P/760 \times 273/T \quad (6)$$

$$\text{Or } (K_0) = L/dt.E \times P/760 \times 273/T \quad (7)$$

where L is drift length, dt drift time, E field gradient, P ambient pressure in Torr or mmHg, and T is temperature (273 K.°). Equation (7) is normally used for routine laboratory work.

IMS is an ionization technique, however due to the interference of $CO_x$ and $NO_x$, it suffers the same difficulties in detecting ozone as the mass spectrometer technique does as described above [33-36]. For this reason, the Global Merit Development is taking a different approach. First it has assembled a reaction sphere in which the neutral reactions thought to deplete ozone can be simulated. Secondly in order to remove the interference of $CO_x$ and $NO_x$, etc, ammonium hydroxide vapor, is introduced into carrier gas inlet system of the reaction sphere as a dopant chemical. By introducing the products of those reactions into the IMS the product ions are detected and identified.

Currently remarkable progress in ultra miniaturization with the technique of FAIMS has been reported [14-16].

Electro Spray Ionization (ESI) technique for mass spectrometry invented in 1989 [50,51] provided an opportunity to analyze large bio molecules by the IMS/MS system for the isomers in particular. The handicap of FAIMS is unable to provide reduced mobility value which is vitally important for identification purpose by the IMS only. A comprehensive review was made on the "IMS as a technique rediscovered for head space vapor site analysis" by Eiceman [52]. Negative ion mode of IMS addresses the same issues as the Electron Capture detector (ECD) together with an additional capability to monitor both negative and positive product ion spectra similar to the APIMS by which the sample molecules can be identified [53].

Significant miniaturization work was achieved by the Bendix corporation (former organization of Smith Detectors) in the period of 1977-1980s [18]. Reasonable trades were made between performance requirement such as sensitivity, selectivity, resolution power, response time, reliability, and repair maintainability for the application. The result was a microprocessor based IMS system which could be operated independent of ancillary gas supplies with selectable specificity. This type of hardware with various chemistries is available from Smiths Detection (USA&UK) and information on similar hardware was reported on [52].

The types of ion/molecule reactions occurring in the reaction region in the IMS can be summarized as follows:

| Positive Ion Mode | Negative Ion Mode |
|---|---|
| Proton Transfer | Electron Capture (associative) |
| $RH^+ + M \rightarrow MH^+ + R$ | $e^- + M \rightarrow M^-$ |
| Ion Attachment | Dissociative Electron Capture |
| $R^+ + M \rightarrow MR^+$ | $R^- (e) + MX \rightarrow X^- + R$ |
| Charge Transfer | Charge Transfer |
| $R^+ + M \rightarrow M^+ + R$ | $R^- + M \rightarrow M^- + R$ |
| | Proton Abstraction |
| | $R^- + MH \rightarrow RH + M^-$ |
| | Ion Attachment |
| | $R^- + M \rightarrow MR^-$ |

Proton transfer reaction: this reaction is accomplished by allowing the protonated trace water reactant ions, i.e. $(H_2O)_n H^+$, to react with the gas phase sample molecules M if the sample molecule has higher Proton Affinity (PA) depending on the sample concentration and relative PA. The PAs of water, acetone, ammonia, and (acetone)$_2$ appear to be 168.9, 193.6, 200.7, and 225.6 kcal/mole. All types of freon gases including CFCs did responded in the positive ion mode with very possibly as MH$^+$ ions in early by PC (IMS) study [8]. Reaction mechanisms for positive ion mode are well described in references of [43-48].

Associative electron capture reaction in the Negative Ion Mode: in the reactor environment of Ni-63/IMS thermal electron, having average energy of 0.5 eV, is captured by sample molecule M to be M$^-$, if the sample molecule has electron affinity (EA) is >0.5 eV. Compounds having slightly higher than 0.5 eV or equal undergo the associative electron capture or resonance capture [31,53]. Ozone molecule having EA 2.103 eV would undergo an associative electron capture reaction in the IMS reactor i.e. $O_3 + e \rightarrow O_3^-$. The Cl. radical formed by the UV irradiation, would undergo interaction with $O_3^-$ i.e. $Cl. + O_3^- \rightarrow O_2 + ClO^-$. Unlike neutral radical, the charged ClO$^-$ energetically is un stable and Cl$^-$ ion takes charge to release the Atomic state O and the Cl$^-$ eventually sink down by forming $(H_2O)_n HCl$. The same is for $(H_2O)_n CO_4$.

Dissociative electron capture: when EA of the sample is considerably higher than the thermal level, the sample molecule capture electron first and subsequently undergo dissociation reaction [53]. For instance the CFC-12, $CCl_2F_2 + e \rightarrow Cl^- + CClF_2$. The fact that EA of Cl, 3.615 eV is higher than EA of F, 3.399 eV and bond energy of C—Cl, 94.3-95.7 kcal/mole, is weaker than that of C—F 132 kcal/mole explains the dissociation capture of Cl atom of Chlorine contained Freon gases but not for fluorine. Similarly compounds contained Bromine and Iodine will undergo dissociated electron capture to form Br$^-$ and I$^-$ respectively. An additional data, in the Positive ion mode, quasi-molecular ion of IMS spectra can be collected for identification.

Charge transfer reaction. When bone dry air is used as a carrier and drift gas in IMS, $(H_2O)_n O_2^-$ is formed along with lesser intensity of $CO_4^-$, $CO_3^-$, $NO_2^-$, Cl$^-$, and OH$^-$. Under these conditions if sample molecules composed with higher EA such as Cl, Br, I, and F are introduced, the negative charge will be transferred to form Cl$^-$, Br$^-$, I$^-$ based on the EA scale.

Proton Abstraction. Because of higher propton affinities of the reactant ions of $(H_2O)n O_2^-$, $CO_4^-$, $CO_3^-$, OH$^-$, and $NO_3^-$, these reactant ions abstract proton from the unsaturated hydrocarbons which has electron withdrawing functional group such as caryophyllens.

negative ion attachment. This is typically accomplished with the reactant ions of $(H_2O)_n O_2^-$, $CO_4^-$, $CO_3^-$, OH$^-$, and $(H_2O)_n Cl^-$. For instance, Cl$^-$ is added to the site of bivalent atom such as sulfur like mustard gas.

DETAILED DESCRIPTION OF THE INVENTION

Experimental Set up.

Our approach is to set up an IMS instrument with which we can perform a simulation work on $O_3$ depletion phenomena in stratosphere at the laboratory conditions. Based on the report of Relativistic Electron Precipitation (REP), the electrons with the energy range of 1-30 MeV in the stratosphere [21-24,30], should produce electrons with energy lower level after interaction with air particles. Thus the environment of stratosphere appears to be similar to the environment of reaction region of the IMS (Ni-source) having electron energy 60 keV-0.5 eV. In order to identify the ions (m/z) produced accurately, ion mass analysis by mass spectrometer is required. A high resolution quadrupole or time of flight mass spectrometry is needed.

Figure 1:
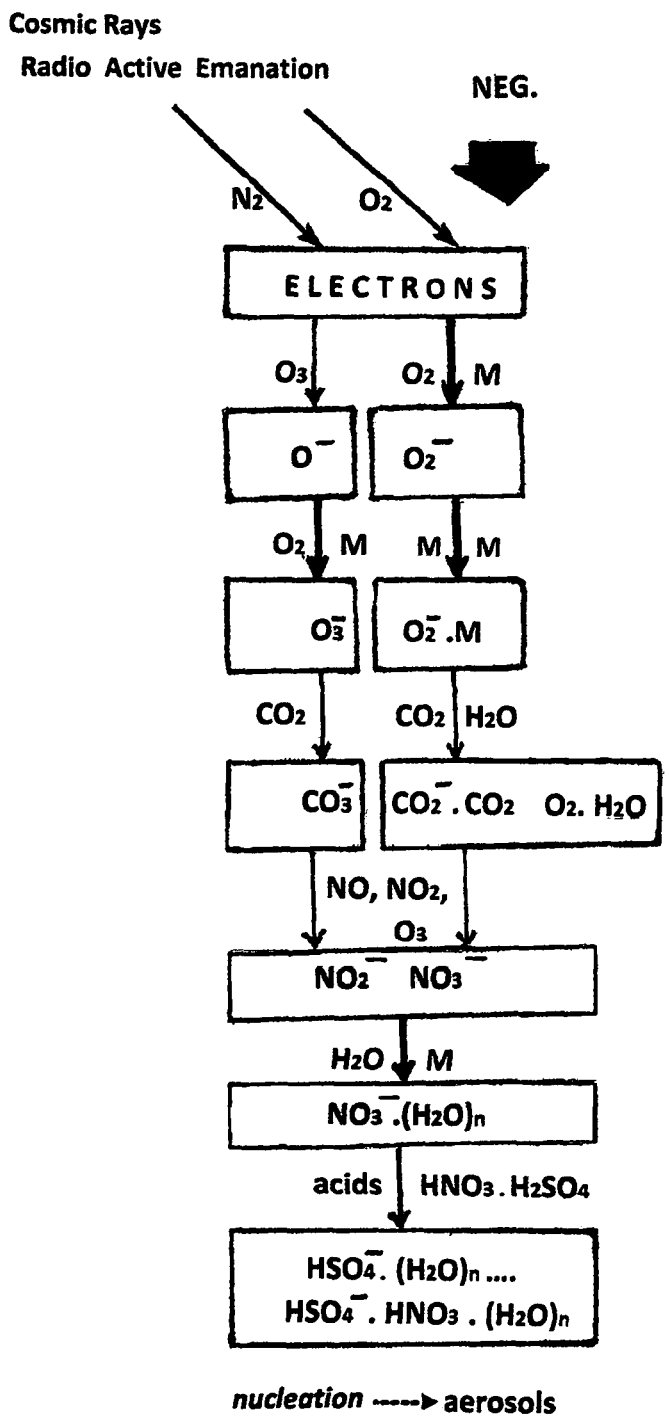
FIG. 1—Ion Chemistry of the lower atmosphere the mesosphere, the stratosphere and the Troposphere.
Figure 2:
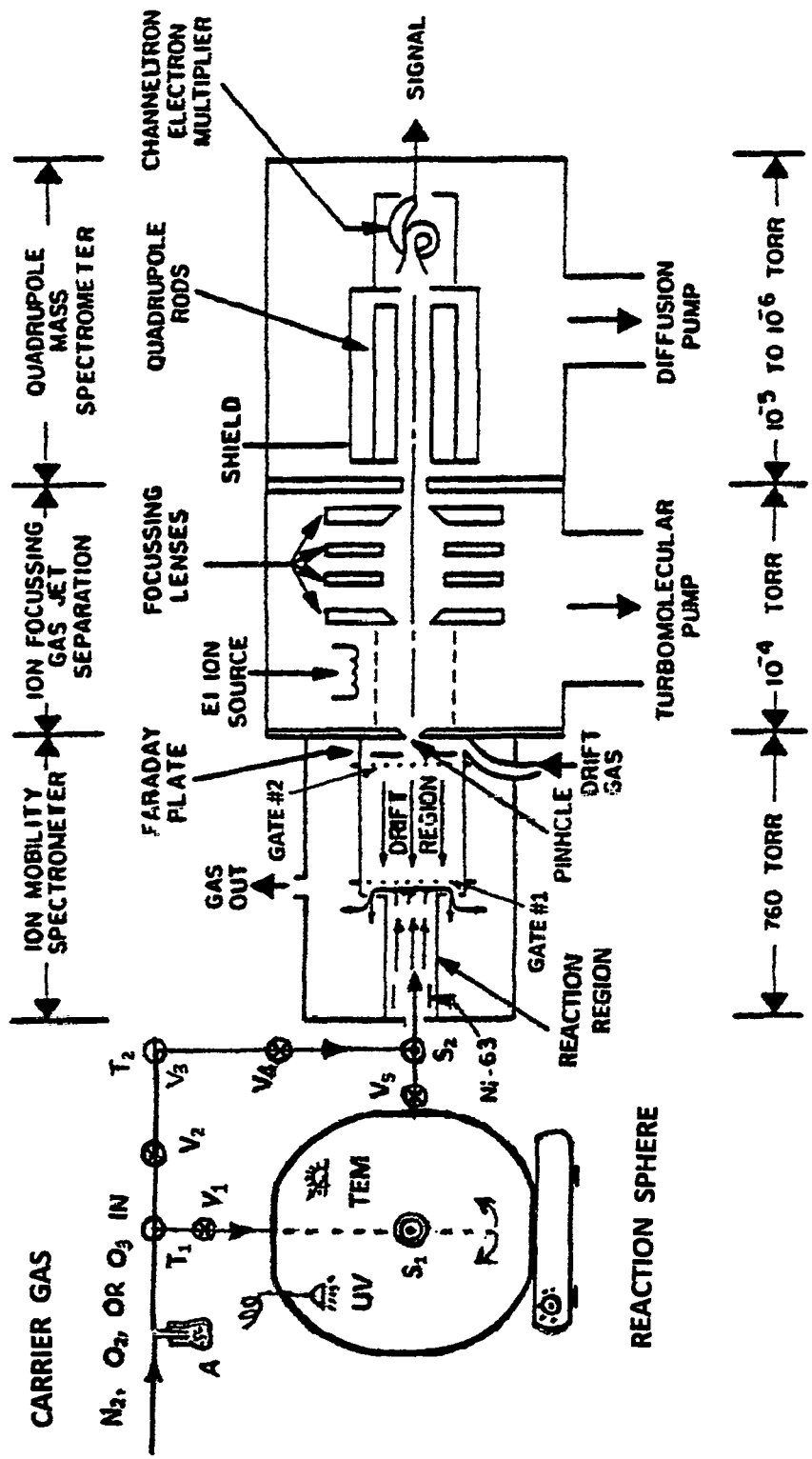
FIG. 2—Schematic Diagram of Ion Mobility/Mass Spectrometer (IMS/MS) System Interfaced with Ion-Molecule Reaction Sphere.

FIG. 2 shows a modified schematic diagram of Ion Mobility Spectrometry/a quadrupole mass spectrometer (IMS/MS)[18, 19] interfaced with a reaction sphere. A reaction sphere can be made by face to face down welding of two St.St steel bowls. Special design has been made to have thermocouple, krypton UV lamp from Solar Light or Cathdeon Ltd. UK, which can scan wave length 175-380 nm range on the top area. Carrier gases such as $N_2$, air, $O_2$, or $O_3$ can be introduced to the reaction sphere by closing valves $V_2$ and $V_4$. Samples of $O_3$ depletion substances can then be introduced to the injection port $S_1$ to perform analysis. The types of collectable data includes: 1) IMS Spectra by only IMS; 2) Total APIMS mass spectra collectable with the two IMS shutter grids open; 3) reconstructed total IMS spectrum by checking of the drift time of individual ions of total mass spectrum. Thus the IMS peak with accurate m/z can be identified. The correlation between IMS and APIMS data can be established for the compounds with interest. Temperature and pressure control, if necessary, can be established in the laboratory conditions.

Using a quadrupole or time of flight mass spectrometer interfaced with IMS/MS system is necessary. The 56 compounds of ozone depletion substances, CFCs or HCFCs [www.epa.gov/ozone/ods.html] [41] can be analyzed with this IMS/MS system. Once the correlation of the IMS and APIMS data is fully interpreted, the library of data file for the algorithm program should be established for the compound identification. These results will verify the IMS alone data file is good enough for monitoring of ozone layer depletion. The reaction sphere can be made for instance by welding two Stainless steel bowls facing down against each other and volume turned out to be 3690 ml. A dopant flask "A" contained with ppm level of ammonium is installed at the entrance of carrier gas line. A neutralization reactions are expected to occur between ammonium hydroxide and acid radicals to precipitate out the radicals of $NO_3^-$, $CO_x^-$, $SO_x^-$. So the reactions of $(NH_4)OH+HNO_3$--->$(NH_4)NO_3+H_2O$. will take place. Similarly $(NH_4)_2CO_4$ and $(NH_4)_2SO_4$ can also take place in the ammonium hydroxide trap before the inlet system.

As a result, the acid radicals which have higher EA value than $O_3$ can be eliminated from the reaction system to pave the way for ozone to be ionized. Now we expect to see a prominent $O_3^-$ IMS peak. Therefore the simulation work of the (e)ion-molecule reaction studies of $O_3$ and related molecules such as CFCs, BrFCs, IFCs, HCFCs, HFCs, and $NO_x$ can be performed with the negative ion mode of IMS or IMS/MS system. Unlike positive ion mode, the response of negative ion mode of IMS is obtainable from only the compounds having polar groups appears to have inherently higher selectivity and lesser interference than the positive ion mode.

Figure 3:
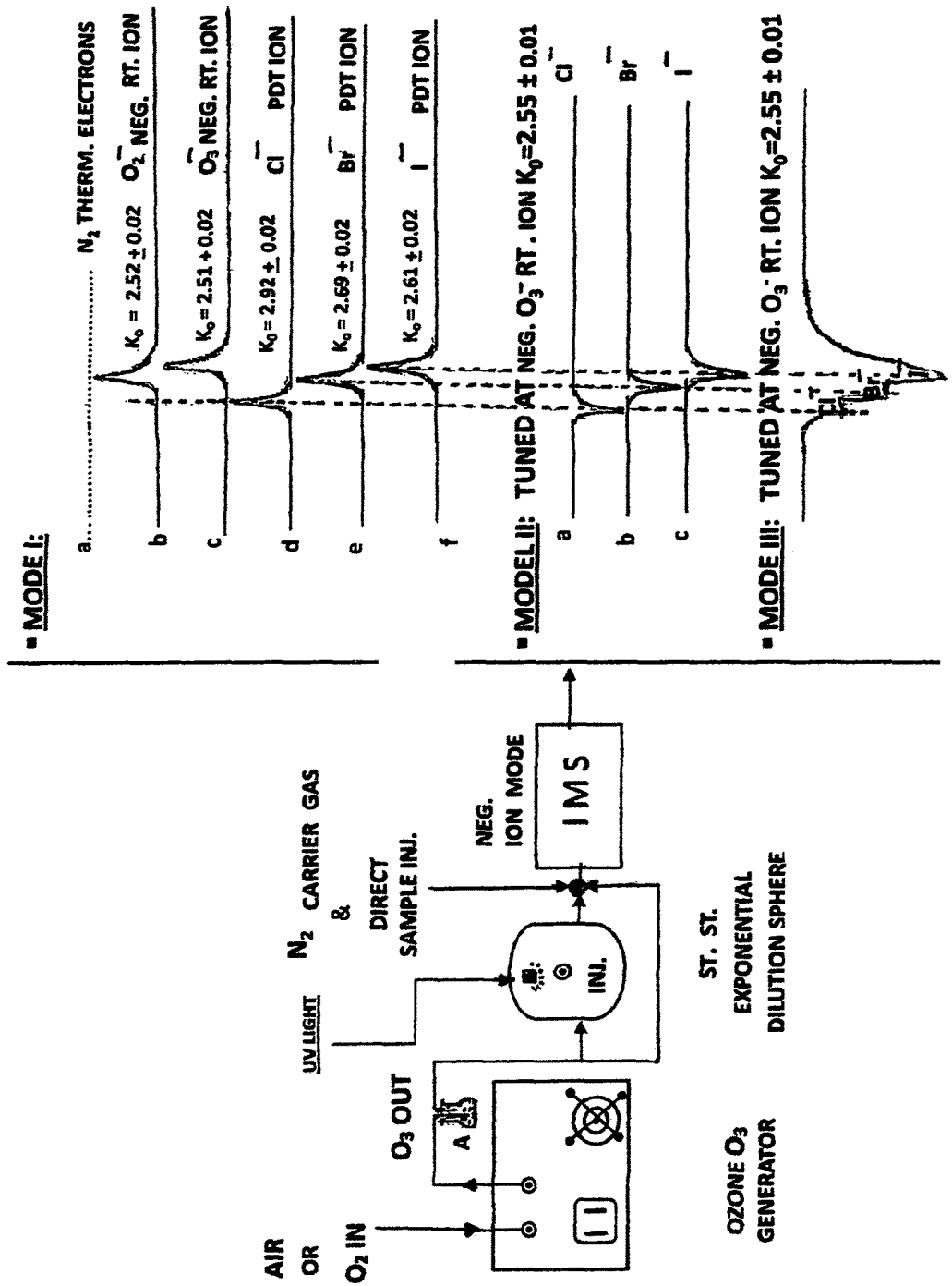
FIG. 3—Schematic Diagram of Negative Ion Mode Mobility spectral data obtainable with IMS/MS using nitrogen, oxygen and ozone carrier gas for the analysis of halide compounds.

FIG. 3 shows a schematic diagram of three modes of ozone depletion monitoring using negative ion mode IMS is shown. The data detected and identified with halide compounds by this system can be collected in three modes.

Mode I: trace a shows standing thermal electron current when $N_2$ is used as carrier gas. In Trace b and c, $O_2$ reactant ion and $O_3$ reactant ion to be formed by injecting 10 ppm level of bone dry air and ozone gas respectively. Reduced mobility $K_o$=2.52 $cm^2V^{-1}s^{-1}$ reported was for the $(H_2O)_n O_2^-$ [53], and 2.55 $cm^2V^{-1}s^{-1}$ [54] within workable error range. The reduced mobility $K_o$ of $O_3$ was reported to be 2.69 $cm^2 V^{-1}s^{-1}$ [55]. Under these conditions, individual halide contained Cl, Br, and I is will be introduced to collect the spectra. Depicted in Traces d, e, and f are the reduced ion mobilities for Cl. Br, I with $K_o$=2.92, 2.61, and 2.51 $cm^2 V^{-1}s^{-1}$ respectively [46, 54].

Mode II: one can simply collect invert spectra of these halides by tuning at the drift time $O_3$ reactant ion. In this operation, the standing current of $O_3^-$ will be decreased down by charge transfer to the halides to become $Cl^-$, $Br^-$, $I^-$ as seen in Traces of a, b, and c in Mode II. These type of operation needs two shutter grids in the drift tube to synchronize open and closing time delay between the two gates.

Mode III: the obtainable spectrum by injecting the mixture of these three different compounds are shown in FIG. 3. The standing reactant ion current will produce spectra responded to these three different compounds as depicted in Mode III. As a result, the individual compound type caused ozone destruction can be identified. The $X^-$ denotes $Cl^-$, $Br^-$, $I^-$ and $F^-$. Fluorine ion however is not observed in IMS condition with probable reasons either high C—F bond energy or too short life time of $F^-$ as discussed above. The capability to provide these three sets of data with ozone depletion substances demonstrate that the negative ion mode of IMS can be developed as a real time monitoring device.

Figure 4:
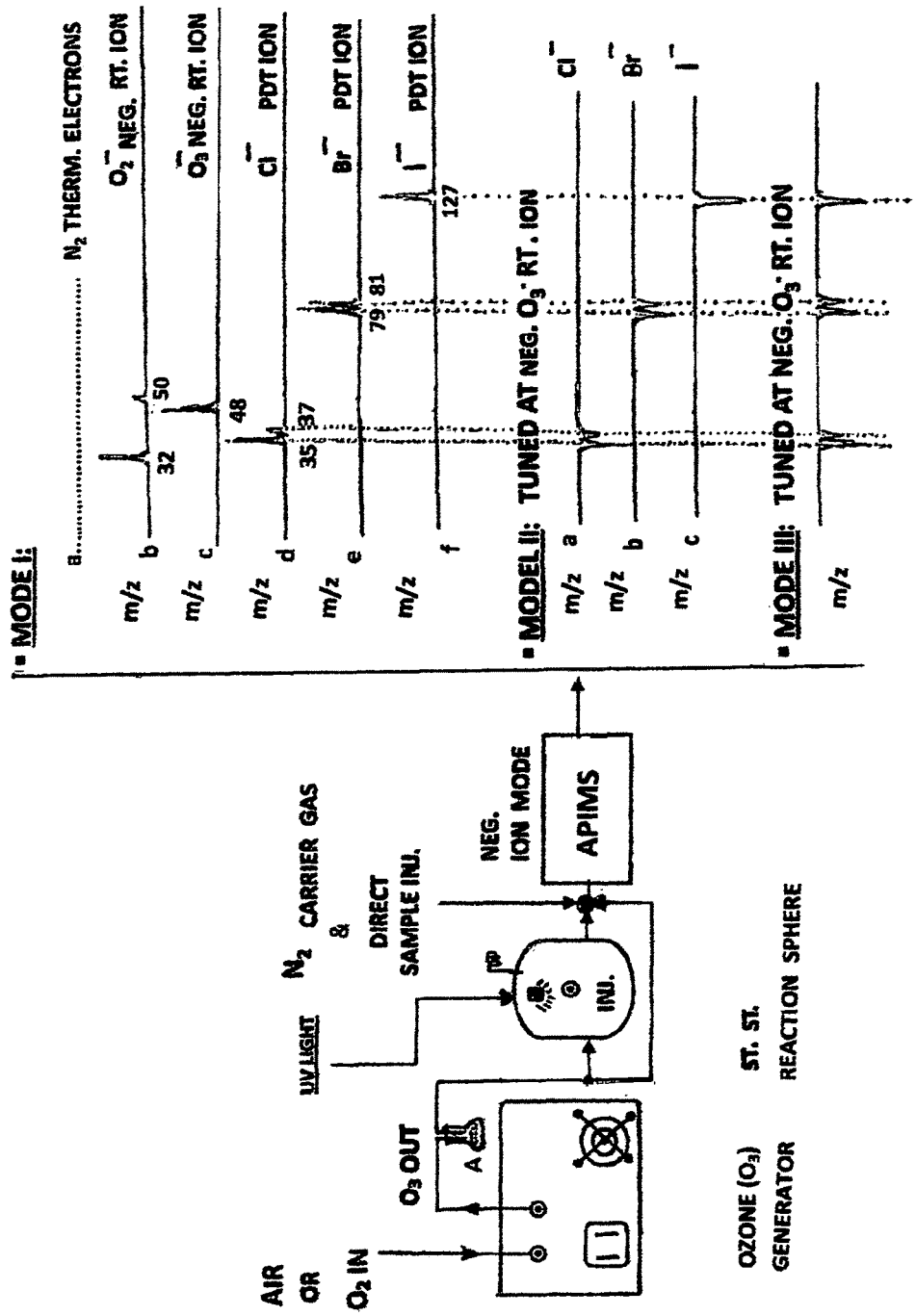
FIG. 4—Product ions spectra of halide compounds from negative ion mode of atmospheric pressure ionization mass spectrometry (APIMS) using oxygen and ozone gas doped into nitrogen carrier gas.

Since the APIMS (=APCIMS) data obtainable from the IMS/MS system shown in FIG. 2, the three Modes of operation illustrated in FIG. 3 also possible with the APIMS system. In FIG. 4, product ions of halide compounds observable by the similar types of modes of operation using negative ion mode of APIMS are shown. In a similar manner as in FIG. 3, data can be produced by mass spectrometer with accurate m/z information of the ions produced shown in FIG. 4.

Using micro syringe if 10-100 ppm level of oxygen ($O_2$) is injected to the reaction sphere through sample injection port $S_1$, one can collect the reactant ion of $(H_2O)_nO_2^-$ with m/z 32 and m/z 50 in weak intensity as shown in Trace b of FIG. 4. Under these conditions, since the EA of $O_3$, 2.103 eV and that of $O_2$, 0.450 eV, with injection of 10-100 ppm of $O_3$ the charge will be taken over by $O_3$ to form the reactant ion of ozone $(H_2O)_nO_3^-$ with m/z 48, as depicted in Trace c of FIG. 4. Since $NO_x$ gases have EA higher than that of $O_3$, $NO_x$ will take over the charge. However $NO_2$ (EA=2.270 eV) or $NO_3$ (EA=3.973 eV) will be removed in the system by the dopant $NH_4OH$ (an acid scavenger), as discussed above. That means in Ni-63 reactor of IMS only air and ozone gas will remain. Under these conditions, the halide compounds (Freon gases) injected in 10-100 ppm level will take over the charge from $O_3^-$ to form $X^-$($X=Cl^-$, $Br^-$, or $I^-$) with m/z 35, 37, for $Cl^-$, m/z 79, 81 for $Br^-$, and m/z 127 for $I^-$ respectively as shown in Trace d, e, and f of FIG. 4.

Based on the data collected throughout the phase I work, additional studies and investigation on the further miniaturization of hardware will be performed. Final design of the ozone monitoring IMS will be made. This Capability to provide the three sets of data with ozone depletion compounds demonstrate that the negative ion mode of the IMS can be developed as a real time ozone monitoring devise at the site of anywhere. This device can be loaded for monitoring $O_3$ in a Balloon, Aircraft, Shuttle, and low orbital Satellite Flight.

Results and Discussion

The Ion Mobility Spectrometry/Mass Spectrometry system is one of the most powerful gas phase analytical systems for the studies of ion-molecule reactions occurring under atmospheric pressure. In the negative ion mode in particular the environment of the IMS (Ni-63) interfaced with the reaction sphere is similar to that of stratosphere as shown in the FIGS. 2-4. As a result, simulation work of ion-molecule reaction studies between $O_3$ and depleting substances such as CFCs, $NO_x$, $CO_x$, $SO_x$, and HCFCs can be performed. Due to tough government regulation on radioactive material handling, IMS with Atmospheric Pressure Corona Discharge Ionization (IMS-APIMS) has been preferred to develop further in trace analysis by researchers in this area. Proton chemistry is dominating in the positive ion mode of both IMS (Ni-63) and IMS-APIMS, while negative ion mode reactant ions of these two IMS systems are different as summarized in Table 2.

by Ewing et al [55]. This is a very good evidence if purer $O_2$ is used the effect of $NO_2$ to block $O_3$ formation is minimal. Under these conditions $O_3^-$ ion would be formed by charge transfer from $O_2^-$ when ppm or higher level of $O_3$ is introduced to the ionization source. Under these circum-

TABLE 2

Comparison of Major Reactant Ion Species of IMS (Ni-63) & IMS (APIMS)

| Ion Source | Pos. RT. Ion | Neg. RT. Ion | Remarks: Carrier Gas |
|---|---|---|---|
| IMS (Ni-63) Ni-63 | $(H_2O)_n NH^4$ $(H_2O)_n NO^+$ $(H_2O)_n H^+$ | Thermal Electrons $(H_2O)_n O_2^-$ $(H_2O)_n O_3^-$, | $N_2$ Carrier & Drift Gas Dry Air Carrier & Drift Gas [54] $O_3$ ppm (2-8 ppm) in $N_2$ *Carr. & Drift Gas Flow. |
| IMS (APCDI) APCDI | $(H_2O)_n H^+$ $(H_2O)_n NO^+$ $(H_2O)_n NH_4^+$ | $O_2^-$, $NO_2^-$, $CO_3^-$, $NO_3^-$ $N_2O_2^-$, $(N_2)O_3^-$, $NO_3^-$ | Dry Air Carr. & Drift Gas [55]. Dry Pure $O_2$ Carr. Drift Gas [56, 57]. |
| IMS (Ni-63), IMS (APCDI) | $(H_2O)_n NH_4^+$ $(H_2O)n H^+$ | $(H_2O)_n O_2^-$, $(H_2O)_n O_3^-$ | $NH_4OH$ Dopant $NH_4^+$ Chemistry $O_3$ 2-10 ppm doped $N_2$ Carrier & Drift gas. |

Note:
*$O_3$ generation with high purity $O_2$ (0.05 ppm of $N_2$ and 200 ppb of $CO_2$) gas. It is predicted to have $(H_2O)n(N_2)mO_3^-$ as reactant ion in this proposal. Results obtained Sabo et al. [56, –60] support this view. The acid radicals such as $NO_3^-$, $CO_3^-$ and $HSO_4^-$ will be precipitated as ammonium salts (Basic Chemistry) [60]. $O_3$ generator available from the Air-Zone Inc. is claimed not to contain any $NO_x$ gas as an impurity in the $O_3$ quality [61, 62].

In Table 2, major reactant ionic species of both positive and negative modes from two different type of IMS-Ni-63 and IMS-APCDI are compared. Ion of $(H_2O)_nH^+$, regardless the kind of carrier gas i.e. $N_2$, Air, or $O_2$, used, is formed as major reactant ion from both IMS-Ni 63 and IMS-APCI. However in the negative ion mode, thermal electron current and $(H_2O)_nO_2^-$ are reactant ionic species for $N_2$ and $O_2$ carrier gas respectively. On the other hand, due to the formation of $NO_x^-$, $CO_3^-$ and $O_3$ gases from corona discharge in the APCDI source, $O_2^-$, $NO_2^-$, $CO_3^-$, (or $N_2O_2^-$), $(N_2)O_3^-$, and $NO_3^-$ are the reactant ionic species observed [53, 56, 58].

Using the reaction rate constant reported (58), k=6.0× $10^{-10}$ cm$^3$/s, from the charge transfer reaction of $O_2^-$+ $O_3 \rightarrow O_3^- + O_2$, reaction time, 9.3 ms was calculated by Ewing et al. [52] for the concentration of $[NO_2]=[O_3]=1.8\times 10^{11}$ cm$^{-3}$ (0.01 ppm as initial concentration) assumed. With the IMS drift time base 20 ms set for the experiment was most reactant ion peaks were observed to be in between 10-15 ms range. This means reaction time range observed for reactant ions were to be within 1-5 ms. As a result, conclusion was made the reaction time of $O_3^-$, 9.3 ms, is too long to be observed in IMS under the conditions they employed. This conclusion seems to be reasonable and understandable. Their initial $O_3$ concentration was assumed to be 0.01 ppm for the above discussion. However the reaction times calculated with 0.02 ppm and 0.1 ppm of the $O_3$ concentration turned out to be 4.8 ms and 0.93 ms respectively. Which means $O_3^-$ very probably should have been observed with the higher concentration of $O_3$.

While even though the EA of $O_3$, 2.103 eV is much higher than that of $O_2$, 0.452 eV. $NO_2$ formed in the APCDI with EA 2,270 eV effectively blocks the formation of $O_3^-$. One more reason is that the faster reaction rate of $O_3^-$+ $NO_2$--->$NO_2^-$+$O3$, k=$7.0\times 10^{-10}$ cm$^3$/s, than that of $O_2^-$+ $O_3=O_3^-+O_2$, k=$6.0\times 10^{-10}$ cm$^3$/s with zero air carrier gas in IMS is responsible for blocking forming of $O_3^-$. With purer oxygen ($N_2$=1 ppm), not zero air, carrier gas $NO_2$ ion is drastically reduced down to ⅓-¼ level of Trace b and only $O_2^-$ ion peak was prominent in intensity in FIG. 3 reported stances, the ammonium hydroxide dopant vapor effectively clean up the $NO_3$ gas to provide an opportunity for ozone to be ionized as $O_3^-$.

The ion species with m/z 60 and Ko=2.52 cm$^2$ V$^-$s$^{-1}$ was interpreted as $CO_3^-$ in their IMS/MS work by Ewing et al. [54] while Sabo et al. [56,59] reported as $(N_2)O_2^-$. The mobility of this ion overlaps the mobility of $O_2^-$ ion peak which is normally prominent negative reactant ion in IMS when zero air is used. Suppose the $(N_2)O_2^-$ is simply a cluster ion formed via the reaction of $O_2^-+N_2 <--->(N_2)O_2^-$ the resultant EA value is predicted to higher than 0452 eV. However The 100 ppt of $CO_2$ in the $O_2$ gas used by Sabo et al. and reported EA value 3.351 eV of $N_2O_2^-$[56], which is rather high, supports the interpretation made by Sabo et al. On the other hand based on data of the intensities of the ions vs discharge time reported by Ewing et al. [55] the ion with m/z 60 is favored to be $CO_3^-$ although the concentration of $CO_2$ was 0.1 ppm in the Zero Air Carrier gas used. With ammonium hydroxide dopant, the ion with $K_0$=2.52 and e/m 60 should be identified correctly.

The ion peaks of $CO_3^-$, $O_2^-$, $NO_2^-$, and $NO_3^-$ appear to have their ion mobility ($k_0$)=2.65, 2.61, 2.83. and 2.56 cm$^2$ v$^{-1}$ s$^{-1}$ respectively [55]. While Sabo et al. [56,57] reported the mobility values of the corresponding similar ion such as $(N_2)O_2^-$ (identical m/z with $CO_3^-$), $O_3^-$, $O_2^-$, and $NO_3^-$ to be $K_0$=2.54, 2.49, 2.44, and 2.14 cm$^2$ v$^{-1}$ s$^{-1}$ respectively. Again ammonium hydroxide dopant will make a lot simpler reactant ion with a clear $K_0$ value and will tell what is the real ionic species responsible for the ion with m/z 60. An application of the technique of FAIMS or DMS [14-16] may give a better resolution of the reactant ions mentioned above. Our future work planned includes the test with FAIMS when the system is available for handling of atmospheric sample analysis [63].

Recently U.S. EPA is considering to bring tolerable ozone level down to 65 ppb level from 75 ppb presently [64]. This policy change is based on the advocates of the public health and environmental activists: ground ozone (bad ozone) is well known to cause coughing, wheezing, asthma attack, and other health threat such as cardiovascular harm, low weight birth, and loss of short term memory as well. On the other hand industries groups strongly oppose the tougher regulation policy. The national manufacturing association (NMA) says the compliance tag of the O3 limit down to 65 ppb level of the U.S. will cause to loose as much as $2.2 trillion annually because of international trade competition power. Under these circumstances, accurate & real time ozone monitoring is vitally important. The real time ozone monitoring proposed in this patent should help policy makers in evaluating the new O3 limit using more accurate ozone concentration in any site.

Functioning at atmospheric pressure conditions, Ion Mobility Spectrometry (IMS) is Capable to detect and identify gas phase chemicals such as warfare agents, explosives, illidit drugs, and ambient air constituents. The negative ion mode in particular, when Ni-63 foil or corona discharge ionization source is used as ionization source, the environment of ionization region appears to be similar to that of the stratosphere. Simulation work on e-molecule reaction and charge transfer reactions occurring in stratosphere therefore can be performed in laboratory conditions. The response mechanism is not only as same as that of gas chromatographic ECD-GC detector but also pave the way to identify chemical identity by providing intrinsic ion mobility value ($K_o$=$cm^2 \cdot v^{-1} \cdot s^{-1}$) difference of the product ions. As a result, scientifically clear pictures of the interactions between ChloroFluoro Carbons (CFCs), Hydro Fluoro Carbons (HFCs), Hydro Chloro Fluoro Carbons (HCFCs), Hydro Chloro Bromo Carbons (HCBrCs), Hydro Chloro Iodo Carbons and Ozone ($O_3$) can be obtained.

As ground based measurement instruments, spectrometers of Gordon Doowbson's Dowbsonometer and Mark III spectrometer have been in use since 1924. Through 1970s, the study of ozone concentration in atmosphere instruments have evolved from ground based spectrometers to balloons, aircraft, rockets, shuttles, and satellites. It measures the total ozone by measuring the relative intensity of the dangerous UVB (wavelength 305 nm) radiation to UVA (325 nm) radiation absorbed by ozone layer using Umker method to deduce vertical $O_3$ distribution. However drawbacks are that it is strongly affected by aerosols and pollutants in the atmosphere because they absorb the UV light at the same wave length region. Recently LIDAR telescope is used to collect UV light that is scattered by two laser beams, one of which is absorbed by ozone (308 nm) and the other is not (351 nm). By comparing the intensity light scattered from each laser, a profile of ozone concentration vs. altitude is measured from 10 to 50 km. The said drawback still exist in this method. These absorption or emission spectroscopy methods are indirect procedure to measure.

The $O_3^-$ formed by capturing electrons via direct e-molecule reaction in the said ozone analyzer of IMS drift through the drift tube to provide its characteristic drift time.

Apparent interference compounds such as $CO_x$, $NO_x$, and $SO_x$ should be completely eliminated by the dopant chemical "ammonium hydroxide solution" installed at the sample inlet line.

Thus the said ozone analyzer IMS not only detect ozone concentration level but also identify the compounds by which the ozone was destroyed in any situs.

Unlike mass spectrometer, the miniaturized IMS instrument is simple to fabricate and able to operate in rugged mobile condition so that real time monitoring of the ozone concentration level is possible not only vertically but also horizontally as well.

REFERENCES

1. J. C. Farman, B. G. Gardiner, S. D. Shanklin, Nature, 315, P. 207-210, 1985.
2. J. Molina and F. S. Roulan, Nature, Vol. 249, No. 3460, June P. 810-812, 1974.
3. Scientific American, September 21, No. 1, 2009, "Ozone Layer Depletion Leveling of"?
4. AnneR. Douglass, Paul A. Newman, and Susan Solomon, Physics Today 67 (7), 42 (2014).
5. Johannes C. Laube, Mike J. Newland, Christopher Hogan, Carl A. M. Brenninkmeijer, Paul J. Fraser, Patricia Martinerie, David E. Oram, Thomas Rockman, Jacob Schwander, Emannuel Witrant, & William T. Sturges, Nature Geoscience, 7, 266-269 (2014) doi: 10.1038/ngeo 2109.
6. S. E. Strahan, A. R. Douglass, P. A. Newman, and S. D. Steenrod, J. of Geophysical Res. Atmosphere, Vol 120, Issue 70, 16 Apr. 2015.
7. A. R. Ravishankara, Andrew A. Turnipseed, Nids R. Jensen, Stephen Barone, Michael Mill, Carleton J. Howard, and Susan Solomon, Science Vol. 263, P. 71-75, 1994.
8. J. E. Loblock, R. J. Maggs, and R. J. Wade, Nature, Vol. 241, P. 194-196, 1973.
9. Stuart P. Cram and Stephen R. Chesler, J. of Chrom. Sci., Vol II, P. 391-400, 1973.
10. G. E. Spangler and Charles I. Collins, Anal. Chem., Vol. 47, No. 3. 1975, P. 393-402, 1975.
11. F. W. Karasek, Oswald Tatone, and David M. Kane, Anal. Chem., Vol. 46, No. 7, P. 1210-1214, 1973.
12. E. P. Grimsrud and D. A. Miller, Anal. Chem., 51, 851, 1979.
13. E. P. Grimsrud and S. H. Kim, Anal. Chem., 51, 537, 1979.
14. Roger Guevremont, J. of Chromgr., Vol. 1058 (1-2), November 26 P. 3-19, 2004.
15. Abu B. Kanu, Dwivedi Prabha; Tam, Maggi; Matz, Laura; Hill, Herb H. jr., J. of Mass Spec., Vol. 43, P. 1-22, 2008.
16. Ashley Wilks, Hart, Machew Hart, Andrew Koehl, Somerville, John Somerviile, Billy Boyle, and David Rutz-Alonso, Int. J. of Ion Mobil. Spec., Vol. 15, 2012, P. 199-222, 2012.
17. F. W. Karasek, S. H. Kim, "Plasma chromatography Sensing Tubes", Final Report, University of Waterloo Research Institute Ontario Canada, Contract #8SUTT-00227, 1980.
18. Glenn E Spangler, D. N. Campbell, K. N. Vora and Carrico, J. P. Carrico, ISA, Transactions, Vol. 23, No. 1, P. 17-27, 1984.
19. Brochure for Phemto-Chem System, PCP Inc., 2155 Indian Rd., West Palm Beach, Fla. 33409.
20. McConnell, John C. McConnel and Jian Jun Jin, Atmosphere Ocean, 46, (1), P. 69-92, 2008.
21. Mansergh Richard Thorne, Science Vol. 195, No. 4275, January, P. 287-289, 1977.
22. A. M. Galper, V. M. Gratcher, V. V. Dmitranco, V. G. Kirillove-Ugryumove, A. V. Orlow, Ulin, S. E. Ulin, and E. M. Shermanon, Int. Union of Pure & Appl. Phys. Burg. Acad. Nana. LCCN, 78-307721, Vol. 12, P. 346, 1997.
23. S. Solomon, and G. Brasseur, Aeronomy of Middle Atmosphere Dovedrecht/Boston/Lancaster/Reidal D. Publishing Co., 1984.
24. N. A. Bui Van, I. M. Martin, A. Turtelli jr. (Brazil), M. I. Fradkin, V. V. Sibikin, Yu. I. Stohzkov, and A. Svirzhevskaya (USSR), I. L. NUOVO CIMENTO Vol. 12C, No. 5 September/October 1989.
25. W. R. Cook, A. C. Cummingo, J. R. Cummingo, T. L. Gerrard, B. Kecman, R. A. Mewardt, R. S. Selesnik, E. C. Stone, D. N. Baker, T. T. Rosenvinge, J. B. Blake, and L.

25. B. Callis, IEEE Transaction on Geoscience and Remote Sensing, Vol. 31, No. 1, May 1993.
26. R. Hossaini, N. P. Chiperfield, S. A. Montzka, A. Rap, S. Dohmas & W. Feng, Nature, Geoscience 8, 186-190 (2015), doi: 10.1038/nge02363.
27. CNE. ACS. 28, Mar. 30, 2015 reportd by Steven K. Gibb.
28. P. Cicman, A. Pele, W. Sailer, S. Matejeik, P. Scheier and Mark, T. D. Mark, Chem. Phys., 371, P. 231-237, 2003.
29. D. D. M. Ho, K. T. Tsang, A. Y. Wong, and R. J. Siverson, UCRL-JC-105225, DE91 002951, Lawrence Livermore National Laboratory, University of California Livermore, Calif. 94550; Science Application International Corporation, Mclean Va. 22103; Department of Physics, University of California, Los Angeles, Calif. 90024.
30. Arther C. Alkin, "Planetary Space Science" Vol. 40, Issue 2-3, February-March, P. 413-431, 1992.
31. Michael T. Bowers, Edited (1979) Gas Phase Ion Chemistry, Vol. 2, 53-86 1979.
32. Q. B. Lu, and L. Sanche, J. of Chem. Phys., Vol. 120, 2434, 2004.
33. D. Smith, P. Spnel, Mass Spectrometry Review, 14 (1995) 255-278, 1995.
34. R. S. Narcisi, A. D. Bailey, L. Della Lucca, C. Sherman, D. M. Thomas, J. Atm. Terr. Phys. 1971, 33, 1147-1159.
35. R. Arnold, J. Kissel, D. Krankowsky, H. Wielder, J. Zahringer, J. Atm. Terr. Phys. 1971, 33, 1169-1175.
36. F. Arnold, G. henschen, Nature, 1978, 257, 521,
37. E. Arus, D. Nevejans, P. Frederick, J. Ingels, J. Atm. Terr. Phys. 1982, 44, 681-694.
38. G. M. B. Dobson Applied Optics, Vol. 7, No. 3, March, P. 387-405, 1968.
39. "Brewer Spectrometer Technical Papers" Courtecy Sci-Tech. Instruments Intl. September 18, Section 1-9, 1996.
40. S. A. Seebrook, J. A. Whiteway, L. H. Gary, R. Staebler, A. Herber, Atmos. Chem. Phys. Discuss., Vol. 13, 1435-1453, 2013.
41. "Ozone in Our Atmosphere" 2010 Update NOAA Earth Sci.; Noaanews.noaa.gov/Stories201; www.albany.edu/faculty/rgk/atm101/ozmeas.htm).
42. PDF Ozone Measurement Earth System Laboratory, www.esl.noaa.gov/escl/assessments/ozone/1994/Chapter 1. Lead Author: N. R. P. Harris, Coauthors: G. Ancellet, L. Bishop, D. J. Hopmann, J. B. Kerr, R. D. McPeters, M. Prendez, W. Randel, J. Staehelin, B. H. Subbaraya, A. Voltz-Thomas, J. M. Zawodny, & C. S. Zerefos.
43. Trends in Ozone Profile Measurements Earth System Laboratory, www.esl.noaa.gov/escl/assessments/ozone/ 2006 Chapter 5, N92-15456, by Panal Members Chair, H. Johnston, A. Akin, R. Nagatani, R. Barnes, W. Planet, S. Chandra, E. Remsberg, D. Cunnold, D. Rusch, J. Deluisi, C. Trepte, J. Gille, R. Viga, R. Hudson, P. Wang, M. P. McCormick, C. Wellemeyer, L. Mcmaster, J. Zowodny, & A. J. Miller.
44. F. W. Karasek, Anal. Chem., 46, 710 A, 1974.
45. S. H. Kim, Fundamental Aspects of Plasma Chromatography and its Application to Analytical Chemistry, Ph. D. Thesis, university of Waterloo, Ontario, Canada N2L 3G1 1977.
46. T. W. Carr, Plasma Chromatography, Plenum Press, new York, 1984.
47. G. A Eiceman and Zeev Karpas, Ion Mobility Spectrometry, CRC Press Inc., 1994.
48. G. A. Eiceman and Zeev Karpas, Ion Mobility Spectrometry, CRC Press Inc., 2005.
49. G. A. Eiceman, Zeev Karpas, Ion Mobility Spectrometry, CRC Press Inc., (Taylor & Francis Group, Boca Raton, Fla.) 2014.
50. J. B. Fenn, M. Mann; C. K. Meng, and C. M. Whiteheuse, Electrospray Ionization for Mass Spectrometry of large biomolecule, Science, 246 (4926); 64-71, Bibcode. Sci., 248-64F. 1989.
51. X. Tang, J. E. Bruce, and H. H. Hill jr., Rapid Commun. Mass Spectrometry, 21 (7) 1115-1122, John Wiley & Son Ltd. 2007.
52. G. A. Eiceman, Anal. Chem., October 1, 435A, Product Reviews Ion Mobility Spectrometry Rediscovered, 2003.
53. F. W. Karasek, and G. E. Spangler, Electron Capture Process and Ion Mobility Spectra in Plasma Chromatography, Edited by Zlatkis, A.; Poole, C. F., Elsvier, 1983, Chapter 15.
54. Francis W. Karasek, Oswald Tatone and David M Kane, Anal. Chem., Vol. 45, No. 7, June 1973.
55. Robert G. Ewing, and Melanie. J. Walton, Int. J. Ion Mobil. Spec., 12: 65-72, 2009.
56. Martin Sab, Jan Palenik, Marek Kucera, Haian Han, Hongmel Wang, Yahnan Chu and Stefan Matejcik, International Journal of Mass Spectrometry, 293 (2010) 23-17.
57. Martin Sab and Stefan Matejcik, Anal. Chem., 83, 1985-1989, 2011.
58. Michael T. Bowers, Edited Gas Phase Ion Chemistry, Vol. 1, Academic Press New York, 1979.
59. Martin Sabo, Jan Matusk, and Stefan Matejcik, Talanta, Vol. 85, 1, 13, July 400-405, 2011.
60. S. H. Kim, Internal Memorandom of Allied Bendix EPID, Identity of Controversial Negative Reactant Ion Peak at drift time 10.52 ms., Feb. 7, 1986.
61. G. Sipos, D. Horvas and A. Dombi, Ozone Science & Engineering, Vol. 18, P. 159-71, 1996.
62. D. W. Arnold and D. M. Newmark, J. Chem. Phys., 102, 7035, 1995.
63. Personal Communication, between Kim, Howard (Global Merit Dev., Inc.) and Boyle, Billy (Owlstone Air Monitoring Nanotech. Inc.) Nov. 28, 2012.
64. ACS Industry Vox Nov. 26, 2014.
65. Joseph E Roehl, Applied Spectroscopy Review, Vol. 26, (issue 1 &2), 1-57, 1991.

The invention claimed is:

1. A method for real time ozone layer depletion in stratospheric conditions monitoring comprising:
   introducing nitrogen carrier gas, ozone and a dopant, ammonium hydroxide vapors, into inlet system for a reaction sphere and reacting to produce pure ozone gas in nitrogen gas stream in reaction sphere; passing said ozone gas into an ion mobility spectrometer coupled to a quadrupole mass spectrometer (IMS/MS) wherein ozone molecule undergoes electron capture reaction with electrons formed by Ni-63 ionization source in reaction region to produce $O_3^-$ which drift through in drift tube and detected by an ion collector plate in said IMS and by electron multiplier in the MS and wherein said IMS/MS operating in negative mode; said ($O_3^-$) ions leftover after depletion by ozone destroying substances being passed into said IMS/MS the resulting ($O_3^-$) spectra thereby simulating ozone layer depletion in stratosphere.

* * * * *